United States Patent

Panescu et al.

[11] Patent Number: 5,916,163
[45] Date of Patent: Jun. 29, 1999

[54] GRAPHICAL USER INTERFACE FOR USE WITH MULTIPLE ELECTRODE CATHETERS

[75] Inventors: Dorin Panescu; David McGee, both of Sunnyvale; Daniel A. Dupree, Saratoga; David F. Dueiri, Santa Clara; David K Swanson, Mountain View; James G Whayne, Saratoga; Robert R. Burnside, Mountain View; Tuan Nguyen, San Jose, all of Calif.

[73] Assignee: EP Technologies, Inc., San Jose, Calif.

[21] Appl. No.: 08/813,624

[22] Filed: Mar. 7, 1997

[51] Int. Cl.$^6$ .................................................. A61B 5/00
[52] U.S. Cl. ........................................ 600/424; 600/374
[58] Field of Search .................................. 600/424, 439, 600/374, 407

[56] References Cited

U.S. PATENT DOCUMENTS

| | | | |
|---|---|---|---|
| 5,265,610 | 11/1993 | Darrow et al. | 128/653.1 |
| 5,341,807 | 8/1994 | Nardella | 128/642 |
| 5,433,198 | 7/1995 | Desai | 128/642 |
| 5,595,183 | 1/1997 | Swanson et al. | 128/697 |
| 5,722,402 | 3/1998 | Swanson et al. | 128/642 |

FOREIGN PATENT DOCUMENTS

| | | | |
|---|---|---|---|
| 0 499 491 A2 | 8/1992 | European Pat. Off. | A61N 1/05 |
| WO95/09562 | 4/1995 | WIPO | A61B 5/05 |

*Primary Examiner*—Marvin M. Lateef
*Assistant Examiner*—Eleni Mantis Mercader
*Attorney, Agent, or Firm*—Lyon & Lyon LLP

[57] ABSTRACT

A graphical user interface (GUI) is provided for assisting medical personnel in interpreting data collected by a multiple electrode catheter deployed within the body. The GUI generates and displays an image of the multiple electrode catheter. By manipulating appropriate controls, the medical personnel are able to change the orientation of the displayed image until it matches the orientation of the actual multiple electrode catheter as seen on a fluoroscope. Afterwards, the medical personnel can determine the relative position and orientation of the catheter by reference to the GUI generated image. To aid in interpreting data recovered by the catheter, the individual electrodes and splines are highlighted and labeled. Electrodes recovering particular types of physiological waveforms can be automatically identified and highlighted. Comments and anatomic landmarks can be inserted where desired to further assist in interpreting data. Views from various, virtual fluoro angles can be obtained, and various images can be recorded, stored and printed. The position of a roving electrode can also be indicated.

25 Claims, 9 Drawing Sheets

Figure 4. (a) Flowchart for the mouse-driven rotation algorithm. (b) Flowchart for the ADD MARKER algorithm. (c) Flowchart for the FIND SITE algorithm.

GRAPHICAL USER INTERFACE FOR USE WITH MULTIPLE ELECTRODE CATHETERS

BACKGROUND OF THE INVENTION

This invention relates generally to Graphical User Interfaces (GUIs) and, more particularly, to GUIs useful in connection with positioning, orienting and operating a multiple electrode catheter within a patient's body for diagnostic, therapeutic or other purposes.

Multiple electrode catheters, such as those shown and described in U.S. Pat. Nos. 5,595,183 and 5,487,391 commonly owned by the assignee hereof, are useful in a variety of medical diagnostic and therapeutic procedures. Such catheters are particularly useful in diagnosing and treating certain cardiac disorders, such as arrhythmias, that can occur for example when localized areas of abnormal tissue within the heart disrupt the normal sinus rhythm.

Today, physicians examine the propagation of electrical impulses in heart tissue to locate aberrant conductive pathways. The techniques used to analyze these pathways, commonly called "mapping," identify regions in the heart tissue, called foci, which can be ablated to treat the arrhythmia.

One form of conventional cardiac tissue mapping techniques uses multiple electrodes positioned in contact with epicardial heart tissue to obtain multiple electrograms. The physician stimulates myocardial tissue by introducing pacing signals and visually observes the morphologies of the electrograms recorded during pacing. The physician visually compares the patterns of paced electrograms to those previously recorded during an arrhythmia episode to locate tissue regions appropriate for ablation. These conventional mapping techniques require invasive open heart surgical techniques to position the electrodes on the epicardial surface of the heart.

Another form of conventional cardiac tissue mapping technique, called pace mapping, uses a roving electrode in a heart chamber for pacing the heart at various endocardial locations. In searching for the VT foci, the physician must visually compare all paced electrocardiograms (recorded by twelve lead body surface electrocardiograms (ECG's)) to those previously recorded during an induced VT. The physician must constantly relocate the roving electrode to a new location to systematically map the endocardium.

These techniques are complicated and time consuming. They require repeated manipulation and movement of the pacing electrodes. At the same time, they require the physician to visually assimilate and interpret the electrocardiograms.

Multiple electrode catheters are effective in simplifying cardiac mapping and ablation procedures. Such catheters make it possible to simultaneously obtain data from several locations within the heart or other organ using a single catheter. During such procedures, the multiple electrode catheter is introduced into a chamber of the heart using known, minimally invasive techniques. The catheter's progress through the vein and into the heart can be followed on a fluoroscope. Radiopaque markers on the catheter enhance the fluoroscopic visibility of the catheter. Once proper deployment within the heart is verified by the fluoroscopic image, localized electrical activity within the heart is monitored by means of the individual electrodes. By noting particular types and patterns of abnormality in the sensed waveforms, the physician is able to identify areas of abnormality in the heart tissue. The abnormal tissues can then be ablated or otherwise treated to remedy the condition.

Various advances in the catheter art now make it possible to include a multitude of individual electrodes (e.g., sixty-four individual electrodes) in a single diagnostic or mapping electrode. It is reasonable to believe that further advances will enable still more electrodes to be used. However, as more and more electrodes are added, it becomes more and more difficult for the attending medical personnel to visualize and interpret the additional data that are made available by such devices. Maximum device effectiveness is realized when the attending medical personnel are able quickly and accurately to visualize the catheter within the body and interpret the information the device is providing. Along with the greater resolution made possible by multiple electrode catheters comes the need for simplified systems and methods of data interpretation.

In one prior data interpretation approach, the various waveforms acquired by the individual electrodes are displayed on a screen. The medical personnel need to mentally integrate the heart activity and position data as displayed on the recorder and fluoroscopy screens in order to assess the health of the underlying tissue. This approach requires a considerable degree of skill and experience on the part of the attending medical personnel. Furthermore, information regarding the relative location of an ablation catheter with respect to the multiple electrodes is not readily available. More significantly, the system becomes impractical and unwieldy as the number of electrodes increases.

In another prior approach, information acquired from a number of sequential locations of a roving electrode is digitally sampled and combined to construct a model "surface" that is displayed on a screen and that visually represents the tissue under consideration. Although much easier to interpret than the prior approach that required mental integration of various inputs, this system, too, provides an unrealistic representation that requires skill and experience to use effectively. Furthermore, the surface is difficult to generate as it requires that a roving electrode be moved over the surface of the heart to reconstruct its geometry point by point. To get reasonable accuracy, a high, sometimes impractical, number of points is necessary.

As the number of electrodes, and, hence, the volume of raw data, increase, it becomes more and more important to display data in a form that can be readily interpreted and understood by the attending medical personnel. Furthermore, it might be desirable to display information in such a way that it can be easily related by the physician to information provided by existing visualization or imaging systems, such as a fluoroscopic system. Visually based systems, which enable such personnel to "see" what is happening, offer a viable means of presenting large amounts of data in a form that can be readily grasped and understood. Graphical user interfaces are one means by which such a goal can be achieved.

SUMMARY OF THE INVENTION

The invention provides a graphical user interface for generating a visual display depicting the relative position and orientation of a multiple electrode catheter within a body. The graphical user interface includes a display screen, an image generator for generating on the display screen an image of the multiple electrode catheter, and a user-actuable control coupled to the image generator for changing the relative position and orientation of the image as displayed on the display screen.

It is an object of the invention to provide a new and improved apparatus for facilitating the interpretation of data acquired through the use of multiple electrode catheters.

It is a further object of the invention to provide a graphic user interface that facilitates such interpretation.

It is a further object of the invention to provide a graphical user interface that enables medical personnel to visualize a multiple electrode catheter in place within a body.

It is a further object of the invention to provide a graphical user interface that can display the location of roving electrodes with respect to the multiple electrode catheter.

It is a further object of the invention to provide a graphical user interface that can be readily implemented on existing computer apparatus.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, wherein like reference numerals identify like elements, and wherein:

DESCRIPTION OF THE PREFERRED EMBODIMENT

Figure 1:
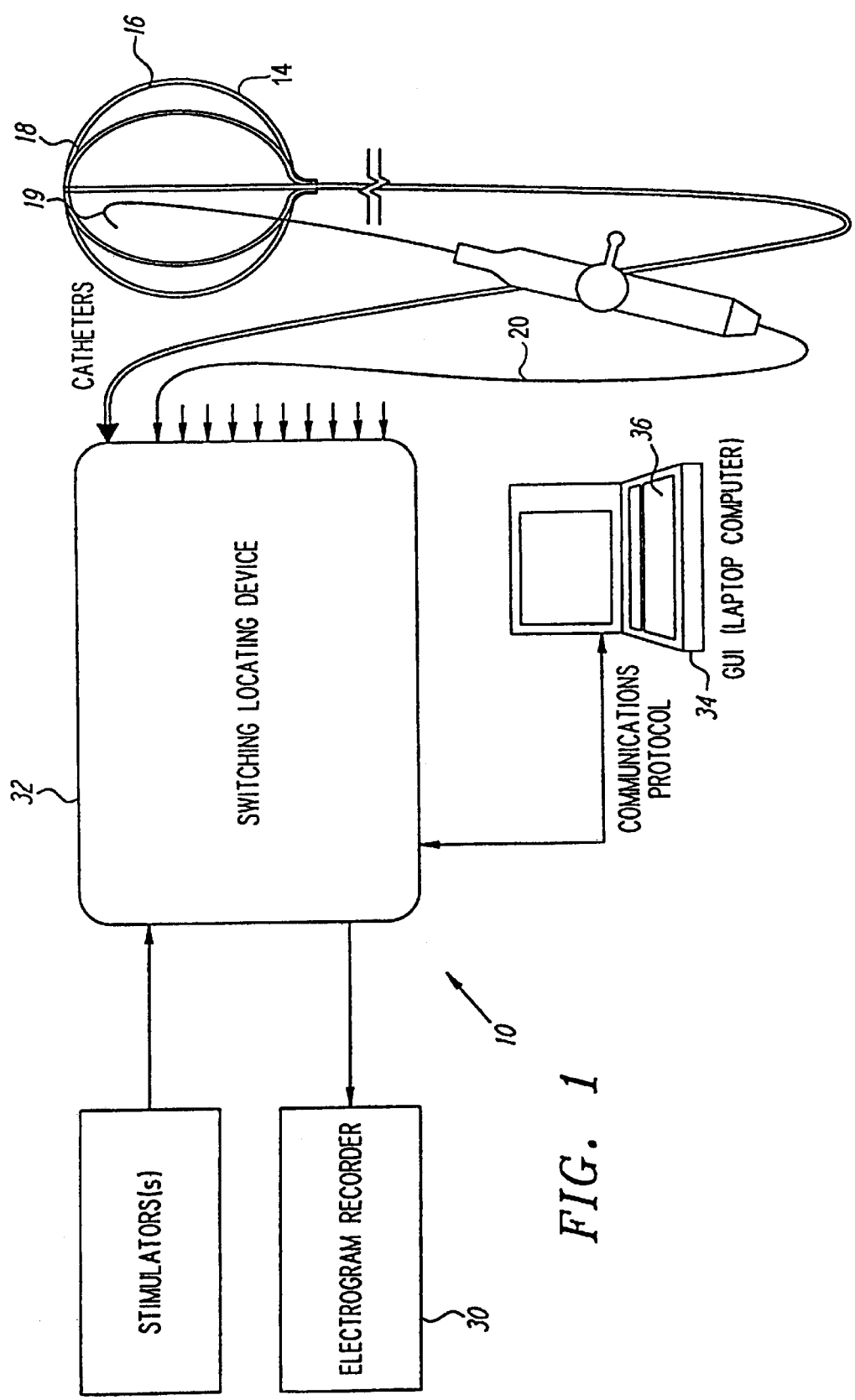
FIG. 1 is a simplified block diagram of a cardiac diagnostic and treatment system having a multiple electrode catheter and a GUI embodying various features of the invention.
Figure 2:
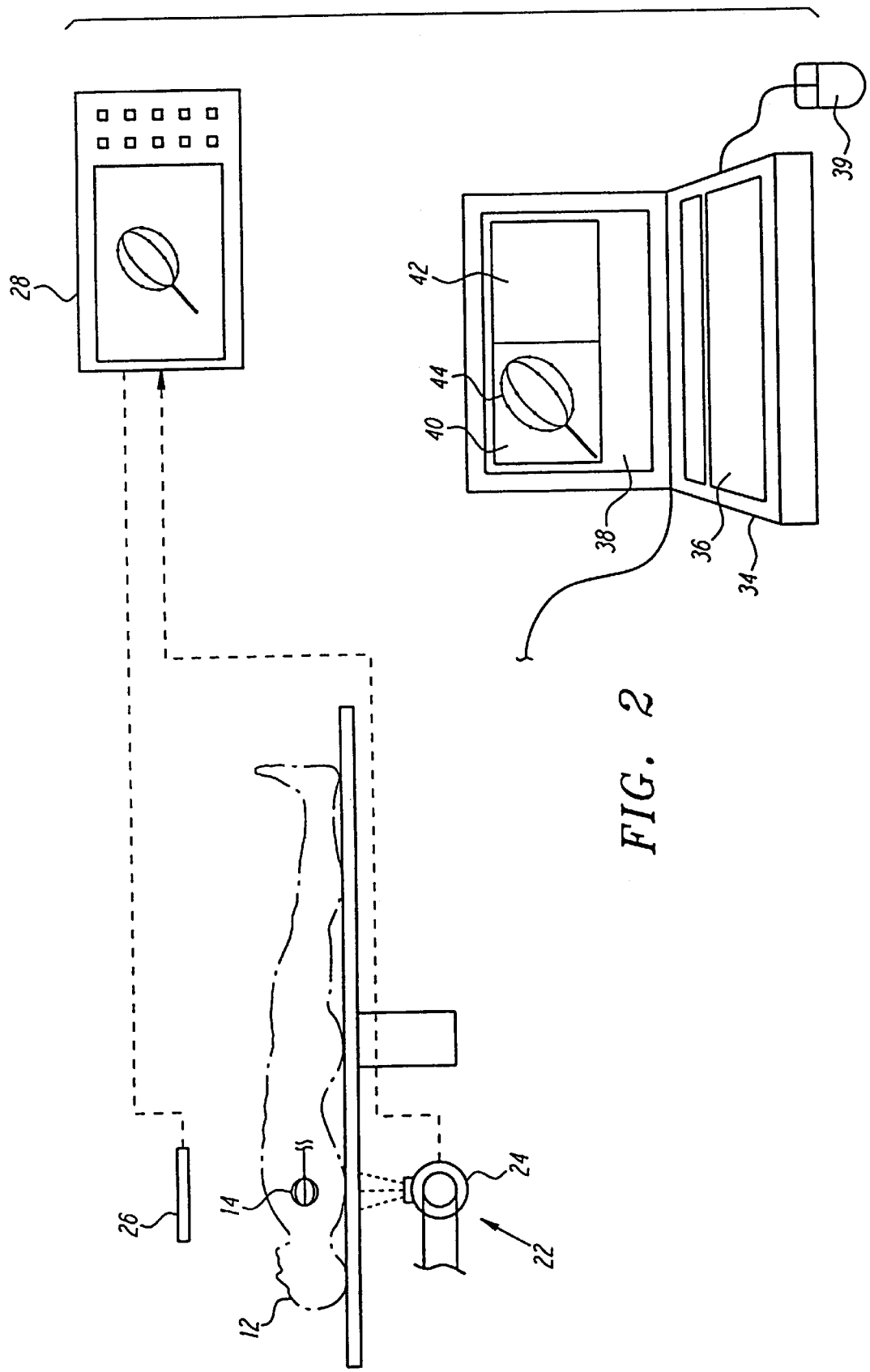
FIG. 2 is a further simplified block diagram of the system shown in FIG. 1 further including a fluoroscope for monitoring the position of the multiple electrode catheter within a patient's body.

Referring to FIGS. 1 and 2, a system 10 for diagnosing, treating or otherwise administering health care to a patient 12 using a multielectrode catheter 14 is shown. In the illustrated embodiment, the system 10 comprises a cardiac diagnostic system that can be used to diagnose and treat abnormal cardiac conditions, such as arrhythmias. It will be appreciated, however, that the system 10 is illustrative and that the invention can be practiced in settings other than cardiac care.

As illustrated, the system 10 includes a multielectrode catheter 14 deployable within the heart of the patient 12. The catheter 14, which can comprise a catheter of the type shown in co-pending application Ser. No. 08/587,251, filed Jan. 16, 1996, entitled Multiple Electrode Support Structure and commonly owned by the assignee hereof, includes up to sixty-four individual electrodes 16 disposed on a plurality of splines 18. Each of the electrodes 16 is connected to an individual conductor in a multiple conductor cable 20. The cable 20 terminates in one or more connectors through which electrical connection can be made to the individual conductors and, hence, to the individual electrodes.

Figure 3:
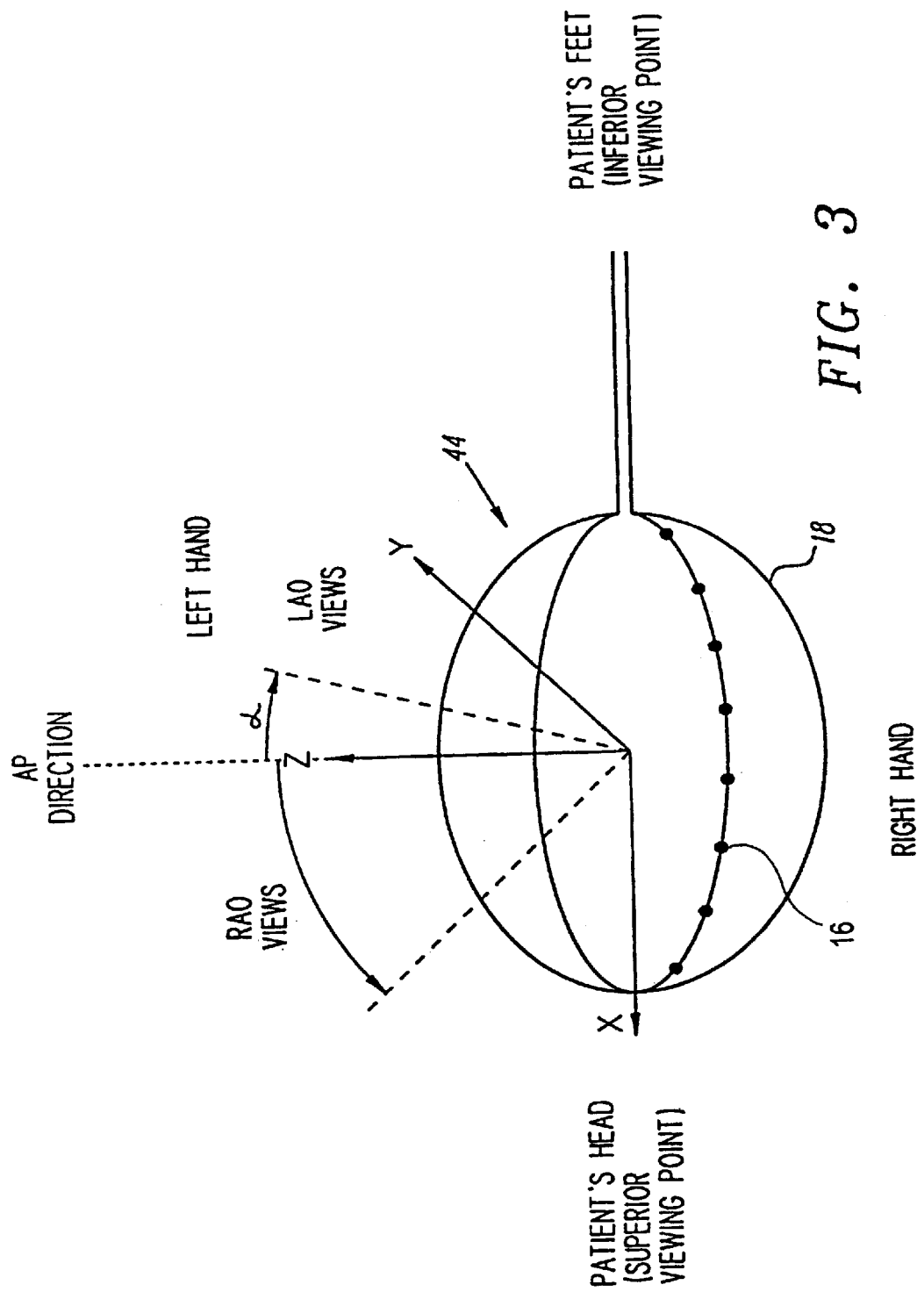
FIG. 3 is a diagrammatic representation of a multiple electrode catheter and a system of coordinates useful in describing positions relative to the multiple electrode catheter.

The system 10 also includes a fluoroscope 22 (FIG. 2) of known construction that can be used to monitor the position of the catheter 14 in the body. The fluoroscope 22 includes a head 24 that generates and directs X-rays into the body, a sensor and an image intensifier 26 that detects the X-rays passing through the body, and a screen 28 that displays the resulting images. The fluoroscope 22 can be rotated around the patient's body to obtain views from different viewing points or "fluoro angles." Certain fluoro angles are more frequently used in the field of fluoroscopy. FIG. 3 illustrates the viewing angles for such views, with respect to the coordinate system associated to the wire-frame representation of the multiple electrode structure. These views are: Right-Anterior-Oblique (RAO) 30 or 45, Anterior-Posterior (AP) and Left Anterior-Oblique (LAO) 30 or 45. The AP View is provided when image intensifier 26 is positioned perpendicular to the patient's chest. The LAO view is provided when the image intensifier 26 is positioned over the left side of the patient's chest. The RAO view is provided when the image intensifier 26 is positioned over the right side of the patient's chest. The angle with respect to the AP orientation is attached as a suffix to the LAO or RAO nomenclature (e.g. if the angle is 30 degrees the view is labeled RAO30 or LAO30). The GUI can also provide virtual views from angles physically unrealized. For example, the Inferior view displays the multiple electrode structure as seen by a viewer looking horizontally from the patient's feet. The Superior view displays the multiple electrode structure as seen by a viewer looking horizontally from the patient's head. The Left or Right 90 views are views orthogonal to the main views AP, RAO or LAO, depending on which view has been selected for display in the left half-screen. For example, if the left half-screen displays a LAO 30 view, Right 90 would be the corresponding orthogonal view and equivalent to RAO 60. Similarly, Left 90 would correspond to LAO 120, although this angle is not physically realizable. Some fluoroscopes include a pair of heads and sensors oriented at right angles to each other. The simultaneous orthogonal views presented by such fluoroscopes further assist the physician in following the progress of the catheter into the patient's body.

The system 10 further includes a biological recorder 30 of known construction that broadly functions to record, store, analyze and display signals acquired by the electrodes 16 of the catheter 14. The biological recorder 30 includes a recording/processing unit that records and processes acquired signals and further includes a display unit that displays the acquired signals to the attending health care personnel.

The system 10 further includes an interface 32 that enables information acquired by the multiple electrodes to be loaded into the biological recorder. To this end, the interface 32 functions broadly to couple individual electrodes or groups of electrodes to the biological recorder. By so coupling the electrodes, it is possible to route all the acquired data into the biological recorder even though the number of available inputs into the recorder may be less than the total number of electrodes.

The interface 32 also applies a known electrical field through the roving electrode 19 and measures the potential distribution generated at the electrodes 16. This information is then used to estimate the location of the roving electrode. A system and method for determining the location of electrode within body has been disclosed in co-pending application Ser. No. 08/745,795 Filed Nov. 8, 1996 entitled "Systems and Methods for Locating Guiding Operative Elements Within Interior Body Regions" and application Ser. No. 08/679,156 filed Jul. 12, 1996 entitled "Systems and Methods for Guiding Movable Electrode Elements within Multiple Electrode Structures" and commonly owned by the assignee hereof. Other methods of localizing electrodes could be employed by the skilled in the art such as presented in prior art U.S. Pat. No. 5,558,091.

The interface 32 is also coupled to an external, user-actuatable, microprocessor-based computer control such as a laptop computer 34 having a keyboard 36 and display screen 38. Preferably, a mouse 39 is included with the computer 34. The interface 32 operates under the command of the computer 34 to interconnect individual electrodes 16 with individual inputs to the biological recorder 30. The Interface 32 also communicates back to the computer 34 information about the location of the roving electrode 19. The computer 34, in turn, responds to requests and instructions entered onto a keyboard 36 by the health care personnel and commands the interface unit 32 to switch among the electrodes 16 as required to achieve the desired function. Commands to configure/test the unified switching system are issued by the computer 34 through the keyboard 36.

A diagnostic and treatment system appropriate for use with the present invention is shown and described, for example, in U.S. application Ser. No. 08/770,971 entitled, "Unified Switching System for Electrophysiological Stimulation and Signal Recording and Analysis," filed Dec. 12, 1996 and commonly owned by the assignee hereof, the specification of which is incorporated by reference herein.

The computer 34 receives roving electrode location information from the interface 32 preferably via a serial bus such as RS 232. The location information can comprise three numbers indicating the 3-D coordinates of the roving electrode. Alternatively, it can be a data stream of 64 bits with one bit corresponding to each of the 64 electrodes 16 of the multiple electrode structure 14. A bit equal to logic 1 indicates that the particular electrode 16 resides at less than a predefined distance threshold (e.g. 2 mm) away from the roving electrode 19. A bit equal to logic 0 indicates that the particular electrode 16 resides at more than the predefined distance threshold away from the roving electrode 19. As such, the approximate location of the roving electrode 19 can be retrieved by knowing in the proximity of which of the electrodes 16 the roving electrode resides.

The invention comprises a Graphical User Interface (GUI) that is implemented on, and resident in, the computer 34. The GUI functions to provide the attending medical personnel with a pictorial or graphic representation of the multielectrode catheter 14 within the patient's body. The various individual electrodes 16 and roving electrode 19 are indicated, as are their locations and orientations relative to themselves. The representation of the multielectrode catheter 14 and/or roving electrode 19 may be manipulated on the display screen 38 until it suggests the orientation of the catheter 14 within the patient's body 12. The orientation may be guided and confirmed by comparing the appearance of the representation of the catheter 14 to the appearance of the catheter on the fluoroscope display 28. Such display helps "orient" the attending personnel with respect to the catheter 14 and the patient's body 12 and thus helps them interpret the data provided by the catheter 14.

The display of the position of the roving electrode 19 helps the physician in guiding diagnosis or therapy application.

The invention makes use of the human ability to process information more readily when presented in a graphic form than when presented as a series of numerical data points. The graphic model of the multielectrode catheter 14 within the body 12 that the GUI provides enables the attending personnel to visualize the locations of the individual electrodes 16 in relation to actual tissue and thus helps the personnel interpret the data obtained by each electrode 16. The GUI further enables the personnel to "turn" their point of view relative to the catheter 14 and the patient 12 and thus "see" the catheter 14 from positions that are not physically realizable. The GUI also enables the personnel to label various electrodes 16, enter notes onto the display 38 and otherwise add visual or informational prompts or cues that further aid in interpreting the information provided by the catheter 14.

The GUI provides a graphical model that represents how a catheter 14 would be situated relative to various anatomical structures if certain assumptions concerning the catheters' location are correct. By reference to this model, the attending personnel are able to visualize were each electrode 16 and spline 18 is located within the patient's body 12.

During a diagnostic or other medical procedure, the fluoroscope 22 is used to monitor the position of the catheter 14. The GUI provides a simplified and idealized representation that supplements the fluoroscopic image 28.

When placed into operation, the GUI displays a simplified, idealized graphical image of the particular type of multielectrode catheter 14 being used in the procedure. In the illustrated and preferred embodiment, the GUI provides a split screen image having a left panel 40 and a right panel 42. A wire-frame image 44 of the catheter 14 appears in standard orientations on both the right and left panels. The particular GUI shown and described is intended for use with a single type of multielectrode catheter 14 of the type shown and described in U.S. Pat. No. 5,549,108 issued Aug. 27, 1996 entitled "Cardiac Mapping and Ablation Systems" and U.S. Pat. No. 5,509,419 issued Apr. 23, 1996 entitled "Cardiac Mapping and Ablation Systems" and commonly owned by the assignee hereof. Accordingly, information regarding the catheter is already retained within the GUI. Alternatively, in other embodiments, the system operators can enter the type of catheter that is being used. The GUI can then display the type of catheter thus selected.

After the initial form of the catheter 14 is displayed, it is necessary next, to set the view in the left panel 40 to match the view of the fluoroscope 28. To this end, the attending personnel compares the fluoroscopic image 28 of the catheter 14 and then manipulates the GUI image 44 on the left panel 40 so that the catheter 44 shown thereon closely matches the live view as seen on the fluoroscopic display 28. To accomplish this, the GUI includes a plurality of on-screen buttons 46 (FIG. 3) that can be pressed to cause the catheter image 44 to rotate. These buttons are the X, Y and Z orientation buttons. These buttons are used to change the relative position of the multiple electrode catheter orientation from its initial position. Thus, the system operator moves the cursor to one of the orientation buttons and presses the left mouse button. This action causes the catheter image 44 to rotate about an idealized coordinate axis 48 located at the virtual multiple electrode catheter center shown in FIG. 3. As to be expected, the X orientation button rotates the multiple electrode catheter image 44 in either a left-to-right or right-to-left direction, the Y orientation button rotates the multiple electrode catheter image in either a top-to-bottom or bottom-to-top direction and the Z orientation button rotates the multiple electrode catheter image in either a clockwise or counterclockwise direction.

Assume a point $P_0$ of coordinates $x_0$, $y_0$, $z_0$ on the envelope surface of the structure 14. After a rotation of angle $\alpha$ about the X axis the new position of $P(x, y, z)$ is given by equation (1).

$$\begin{bmatrix} x \\ y \\ z \end{bmatrix} = \begin{bmatrix} 1 & 0 & 0 \\ 0 & \cos(\alpha) & \sin(\alpha) \\ 0 & -\sin(\alpha) & \cos(\alpha) \end{bmatrix} \cdot \begin{bmatrix} x_0 \\ y_0 \\ z_0 \end{bmatrix}$$

Equation (2) and (3) define rotations of angle $\alpha$ about the Y and Z axis, respectively:

$$\begin{bmatrix} x \\ y \\ z \end{bmatrix} = \begin{bmatrix} \cos(\alpha) & 0 & \sin(\alpha) \\ 0 & 1 & 0 \\ -\sin(\alpha) & 0 & \cos(\alpha) \end{bmatrix} \cdot \begin{bmatrix} x_0 \\ y_0 \\ z_0 \end{bmatrix}$$

$$\begin{bmatrix} x \\ y \\ z \end{bmatrix} = \begin{bmatrix} \cos(\alpha) & \sin(\alpha) & 0 \\ -\sin(\alpha) & \cos(\alpha) & 0 \\ 0 & 0 & 1 \end{bmatrix} \cdot \begin{bmatrix} x_0 \\ y_0 \\ z_0 \end{bmatrix}$$

In general, if a sequence of X, Y, or Z rotations is performed, the final coordinates of the point P depend on the exact order the rotations are performed in.

Figure 4A:
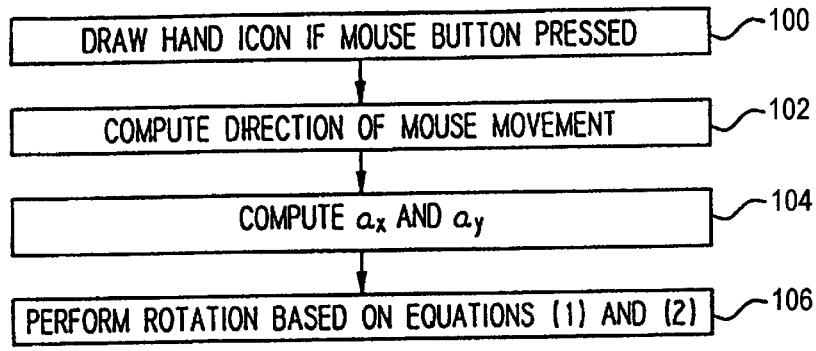
FIG. 4(a) is a flowchart diagram useful in understanding an algorithm used to rotate a wire-frame display of a multiple electrode structure using a mouse.

Alternatively, the system operator may utilize the mouse controls to rotate the multiple electrode catheter image. Whenever the cursor is positioned in the left panel 40 and the left mouse button is pressed, the cursor changes from an arrow-style image to that of a hand-style image 50. This action causes the movement, that is to say, the rotation of the multiple electrode catheter image in response to the movement of the mouse by the system operator. By keeping the mouse left button pressed, the system operator may position the multiple electrode catheter image. When the left mouse button is released, the multiple electrode catheter image 44 remains in the current orientation. FIG. 4(*a*) presents the flowchart of the algorithm for the mouse-driven rotation. Element 100 draws the hand icon when the mouse button is pressed. Element 102 computes the direction of mouse movement. Based on this information, element 104 computes two rotation angles about the X and Y axes. Element 106 performs the actual rotation based on equations (1) and (2) above. The action of rotating the wire-frame multiple electrode catheter representation 44 in the left panel 40 by means of X, Y and Z orientation button or mouse movement may be repeated until the system operator is satisfied with the orientation of the multiple electrode catheter image in reference to the fluoroscopic image 28.

Preferably, the wire-frame representation 44 of the multiple electrode catheter 14 shows a plurality of splines 52 corresponding in number to the actual number of splines 18 used in the multielectrode catheter 14 and further shows a plurality of electrodes 54 on each spline 52 corresponding in number to the actual number of electrodes 16 on each spline 18. In the preferred embodiment, splines 52 and electrodes 54 on the wire-frame image 44 are highlighted, colored differently, sized distinctly or otherwise distinguished visually from the others to provide a representation of the multiple electrode catheter in a virtual three-dimensional space where the center of the wire-frame model 44 is designated as the center of that three-dimensional space. In the illustrated embodiment, the wire-frame image 44 is generated such that splines 52 and electrodes 54 which lie in the background of the three-dimensional space (i.e., behind the center of the three-dimensional space as viewed from the system operator's viewing angle) appear darker or shadowed compared to the splines 52 and electrodes 54 appearing in the foreground. This enhances the three-dimensional appearance of the multiple electrode catheter image 44 on the screen 38.

Once the orientation of the virtual multiple electrode catheter image is matched to the real fluoroscopic image, as viewed by the system operator, it may be saved or stored in the computer memory by pressing the "Save View" button. The "Save View" button provides for the system operator to save or store the current multiple electrode catheter image as any of the standard views, i.e., the "AP", "LAO45", "LAO30", "RAO30" OR "RAO45" views.

To further assist the operating personnel in interpreting what they see, it is frequently helpful to provide other viewing angles that are related to the standard fluoroscopic view but not realizable by such equipment. To this end, the GUI based on the properly orientated image shown in the left panel of the display, is operable to generate and display multiple electrode catheter images in the right panel that are orthogonal to the view in the left panel. Such orthogonal views are displayed in the right panel relative to the view set in the left panel.

In the illustrated embodiment, the GUI provides orthogonal views calculated from the "Superior", "Inferior", "Left 90" and "Right 90" views.

Preferably, the wire-frame representation 44 of the multiple electrode catheter 14 shows a plurality of splines 52 corresponding in number to the actual number of splines 18 used in the multielectrode catheter 14 and further shows a plurality of electrodes 54 on each spline 52 corresponding in number to the actual number of electrodes 16 on each spline 18. Preferably, one or more of the splines 52 or electrodes 54 is highlighted or otherwise distinguished visually from the others to provide a reference for orienting the displayed wire-frame image 44. In the actual catheter 14, one or more of the splines 18 or electrodes 16 are provided with a fluoroscopic marker that appears on the fluoroscope screen 28 and that serves to identify a particular one of the electrodes 16 for reference purposes. The electrode 60 highlighted by the GUI corresponds to this electrode and is positioned to closely match the position of the corresponding electrode on the fluoroscope screen 28.

The described procedure thus coordinates the "three dimensional" wire-frame multiple electrode catheter representation 44 generated and displayed by the GUI with the two dimensional display of the actual multiple electrode catheter 14 shown on the fluoroscope screen 28.

After the displayed multiple electrode catheter image 44 is properly oriented, the view can be saved by clicking the "Save View" and "OK" buttons that appear on the display screen 38.

In the illustrated embodiment, the wire-frame image 44 generated on the left panel 40 of the display 38 corresponds to the view of the multiple electrode catheter 14 displayed on the fluoroscope screen 28. To further assist the operating personnel in interpreting what they see, it is frequently helpful to provide other views that are not easily realizable using the fluoroscopic equipment 22. To this end, the GUI, based on the properly oriented image 44 shown on the left panel 40 of the display 38, is operable to generate and display images 44' of how the multiple electrode catheter image 44 would appear if view from other angles. Such alternate views are displayed on the right panel 42 of the display 38.

In the illustrated embodiment, the GUI provides "Superior," "Inferior," "Left 90°" and "Right 90°" views. These views are obtained by clicking the appropriately labeled corresponding buttons on the screen 38. The image appearing on the right panel 42 of the display 38 tracks the orientation of the image 44 on the left panel 40. Thus, if the image orientation on the left display panel 40 is changed or adjusted, the right image 44' will also change to reflect the new orientation of the catheter 14 relative to the body.

In the illustrated embodiment, fluoro angles between −90° and +90° can be used and can be entered into the GUI. Thus, the GUI can be still be effectively used if, for some reason, the attending personnel elect to position the fluoroscope to a non-standard fluoro angle. In the illustrated embodiment, views at the standard fluoro angles of −45°, −30°, 0°, +30° and +45° can be automatically saved. Customized views at non-standard fluoro angles can also be named and saved.

As previously mentioned, the primary function of the GUI is to provide a visual image or model 44 that assists the operating personnel in visualizing the multiple electrode catheter 14 within the patient's body 12 and interpreting the data acquired from the multiple electrode catheter 14. Although this is largely achieved by orienting the wireframe display representation of the electrode basket to match the actual image provided by the fluoroscope, the GUI provides several additional functions that further enhance its effectiveness. Various of these additional functions are described below.

A MARKERS function is provided which enables the operator to alter and enhance the displayed multiple electrode catheter wire frame image. The MARKERS function includes an ADD MARKER function that enables the operator to add an identifier or marker to selected locations of the electrode image 44 displayed in the left screen 40. This function is useful if the operator wishes to mark selected locations that are significant or of interest, such as mapping sites, ablation sites, etc. By having such sites highlighted or otherwise distinguished, the operator is better able to remain coordinated and oriented with the displayed image and, therefore, better able to interpret data recovered by the multiple electrode structure. The markers appear on the surface defined by the various splines 52.

Figure 4B:
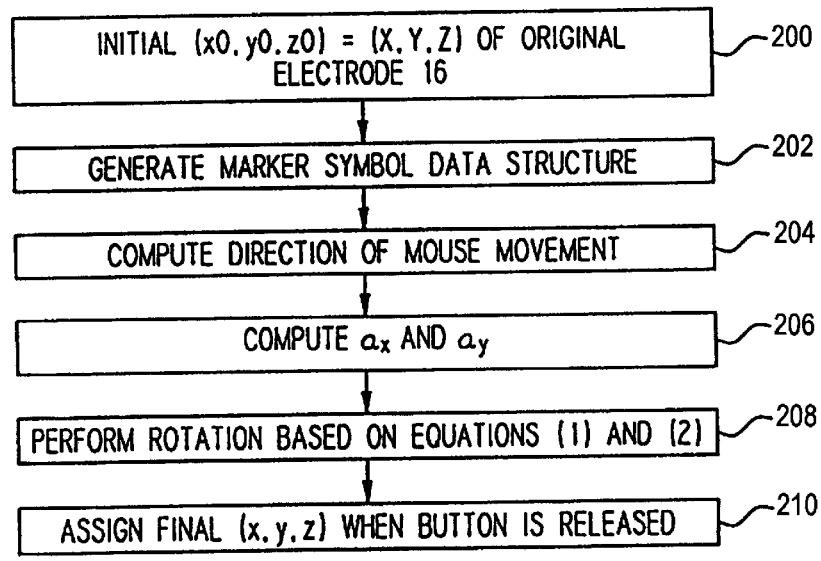
FIG. 4(b) is a flowchart diagram useful in understanding the operation of an algorithm used to identify user-requested electrodes within the wire-frame display of the multiple electrode structure.

The MARKERS function is used by clicking the ADD MARKER button that appears on the screen after the general "MARKERS" button is clicked. Pressing the right mouse button on an electrode causes a marker to appear on the screen. With the right button thus depressed, the mouse is used to "drag" the marker over the implied surface of the multiple electrode catheter to the desired location. When the right button is released, the marker is "dropped" into the desired marker location. Markers can thus be placed near electrodes on either the foreground or background of the multiple electrode catheter. FIG. 4(b) shows the flowchart of the algorithm used to add markers. Element 200 assigns the initial $x_0$, $y_0$, $z_0$ coordinates of the marker when the mouse button is pressed. These initial coordinates are identical to those of the electrode 16 acting as origin of the placement. Element 202 generates the marker symbol and inserts the corresponding software data structure into a linked list. Element 204 computes the direction of the mouse movement based on information received from the mouse port. Element 206 converts the direction information into two rotation angles, about the X and Y axes, respectively. Element 208 computes the new location of the marker based on equations (1) and (2). Element 210 assigns the final x, y, z coordinates to the marker when the mouse button is released. Markers are created as data structures comprising: pointer to previous marker, order number, coordinates, comments, time stamp and pointer to next marker.

Also included in the MARKERS function is a COMMENT function that enables the operator to add custom notes or comments to each marker. For example, if the operator wishes to comment on the significance of each selected, marked site, the COMMENT function can be used for this purpose. A COMMENT window appears as soon as the marker is "dropped" at the selected site. A time stamp is preferably included in the comment. The operator can enter the desired comment into the comment window using the computer keyboard. By clicking the OK button, the comment thus entered is saved. If no comment is desired, the CANCEL button can be clicked. A PREV. COMMENT button is provided which, when actuated, displays comments previously entered with earlier markers. A NEXT COMMENT button displays comments associated with later entered markers. Once a marker is "dropped," its comments can be retrieved by placing the cursor onto the marker and pressing the right mouse button.

A DELETE MARKER function is provided for deleting previously entered markers. This function is actuated by clicking on the DELETE MARKER button and thereafter placing the cursor on the desired marker. When the right mouse button is pressed, the selected marker is deleted. When a DELETE operation is performed the corresponding marker data structure is removed from the linked list by employing well-known data structure software techniques.

The MARKERS function is terminated by clicking the CLOSE button.

The GUI also provides a mapping function that enables the operator to create any of five types of binary maps. The available mapping functions are (1) EARLY ACTIVATION, (2) FRACTIONATION, (3) GOOD PACE MAP, (4) CONCEALED ENTRAINMENT and (5) USER DEFINED and are characterized as follows:

EARLY ACTIVATION. The EARLY ACTIVATION mapping function identifies and marks the electrodes where early depolarization of the heart tissue has occurred. Early depolarization is often an indicator of abnormal heart tissue adjacent the electrode.

FRACTIONATION. The FRACTIONATION mapping function identifies and marks the electrodes where the electrograms sensed by such electrodes appear fractionated or broken in appearance. Again, the existence of fractionated electrograms a particular electrode site is often an indicator of abnormal cardiac tissue at that site.

GOOD PACE MAP. The GOOD PACE MAP mapping function identifies and marks the electrodes with high pace mapping matching index. This index reflects how many of the morphologies of 12-lead surface electrocardiograms (ECG) acquired during non-induced arrhythmia match the morphologies of the same signals acquired during paced induced arrhythmia from the particular electrode. If by pacing from a particular electrode 16, a high number of the 12-lead ECG morphologies are similar during non-induced and pace-induced arrhythmia then it is likely that the particular electrode 16 resides close to an arrhythmogenic focus.

CONCEALED ENTRAINMENT. The CONCEALED ENTRAINMENT mapping function identifies and marks the electrodes where arrhythmia entrainment was achieved. Abnormal cardiac tissue often is located electrodes exhibiting CONCEALED ENTRAINMENT.

USER DEFINED. The USER DEFINED mapping function enables the user to specify particular criteria to be used for categorizing signals obtained by the multiple electrodes. Electrodes providing signals meeting the selected criteria are identified and marked. The USER DEFINED mapping function allows the physician to locate areas of cardiac tissue exhibiting certain preselected characteristics and further enhances the diagnostic function of the system.

The various mapping functions are of importance in identifying potential ablation sites. Frequently, abnormal cardiac tissue, which can be effectively treated through ablation, often exhibits more than one abnormal characteristic. Such sites frequently appear on two or more of the EARLY ACTIVATION, FRACTIONATION and CONCEALED ENTRAINMENT maps. If the same electrode or groups of electrodes appear on two or more of the ACTIVATION, FRACTIONATION, GOOD PACE MAP and CONCEALED ENTRAINMENT maps, a likely site for ablation is particularly well indicated.

Numeric values, such as activation time numbers, cardiac signal voltages, or propagation velocities, can be associated to each electrode of the multielectrode catheter structure. Then, isovalues (i.e., isochronal, isopotential, isoconduction etc.) can be generated. The iso-value maps can be used in association with the binary maps, markers and anatomic features to further identify potential ablation sites.

The mapping function is initiated by clicking the CREATE MAP button that appears on the display screen. When this button is clicked, a popup window appears offering a choice of any of the five mapping functions. By clicking on the selected choice, the desired mapping function is initiated.

After the desired mapping function is selected, the mouse is used to drop binary map markers at the electrodes of interest. This is done by moving the mouse to place the cursor over the electrode of interest and then depressing the right mouse button to drop the marker at the selected electrode. The algorithm for generating binary map markers is substantially similar to that shown in FIG. 4(b). The only difference is that the rotation step 208 is not performed. The binary map markers are directly attached to the selected electrode 16. Similar data structure techniques are used to create and update the required binary map linked lists. The data structure corresponding to a binary map marker comprises: pointer to previous marker, electrode number, binary map type, comment, time stamp, iso-value type and pointer to next marker. After the selected electrodes are thus marked, a different type of binary map can be selected or the CLOSE button appearing on the pop-up window can be clicked. Specific comments can be entered by the operator using the computer keyboard. If the comments are acceptable, the OK button is then clicked. If not, the CANCEL button is clicked and the comments are not saved. Comments can later be retrieved by placing the cursor over a binary map marker and then pressing the right mouse button.

Various other functions are provided in connection with the mapping function. A SHOW MAP function can be selected by clicking the SHOW MAP button. This function displays the types of binary maps that are available. By clicking on one of the listed types, the selected binary map will then be displayed. The types of maps being displayed will be indicated with a check mark (✓).

A CLEAR MAPS button functions, when clicked, to delete and clear all existing binary maps.

A REMOVE MAP POINTS button operates, when clicked, to clear a specific map point by placing the cursor on the map point to be removed and clicking the right mouse button.

A CLOSE button functions, when clicked, to close the BINARY MAP function.

Still additional functions are provided by the GUI.

A FEATURES function displays a pop-up window with choices for anatomic markers. The anatomic markers function to indicate on the display the location of certain anatomic structures or landmarks (e.g., the aortic valve, the inferior vena cava, the superior vena cava etc.) relative to the multiple electrode catheter. Having the relative locations of such anatomical structures displayed relative to the multiple electrode catheter and its other features helps the physician in guiding the catheter, and in mapping and treating the cardiac tissue.

To operate this function, the FEATURES button is clicked, which causes a pop-up window to be displayed. The window displays a number of choices for anatomic markers. The desired anatomic marker is selected using the cursor, and the marker is then dragged to the desired location using the right button of the mouse. At the desired location, the right mouse button is released to drop the marker at the desired location. The algorithm which inserts these anatomic markers works similarly to that shown in FIG. 4(b). However, the anatomic markers are not created as linked lists data structures. The anatomic markers can be deleted as a group by clicking on the CLEAR ALL FEATURES button, or can be selectively deleted by clicking the REMOVE FEATURE button.

A PRINT function can be selected by clicking on the PRINT button. This function prints both multiple electrode catheter views plus current and existing comments on the system's default printer.

A SAVE VIEW function saves the selected principal view (i.e., the left screen panel) when actuated. All other views are updated accordingly.

A SHOW SPLINES function labels the individual splines of the electrode basket when actuated. This button also turns into HIDE SPLINES to facilitate label removal when desired. Spline labels in the foreground appear brighter than spline labels in the background to further enhance the three-dimensional effect provided by the GUI.

Figure 4C:
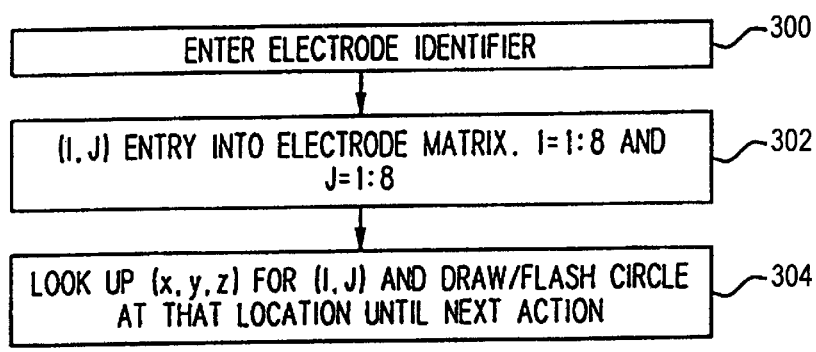
FIG. 4(c) is a flowchart diagram useful in understanding the operation of an algorithm used to associate markers or anatomical features with the wire-frame display of the multiple electrode structure.
Figure 5:
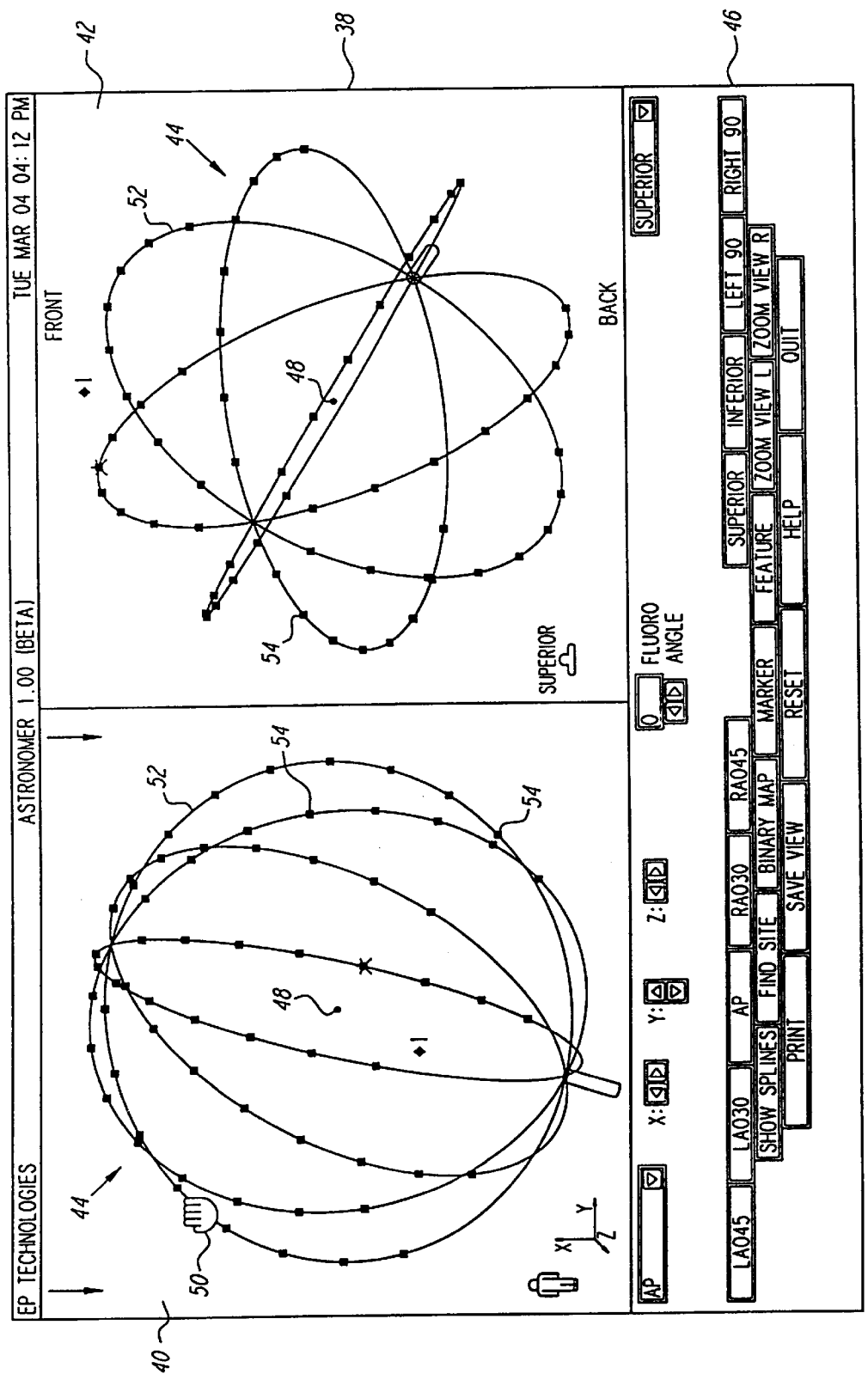
FIG. 5 is a sample of a display screen generated by the GUI, useful in understanding the look and feel thereof.

A FIND SITE function operates, when actuated, to enable the operator quickly to locate a particular electrode. When this function is actuated, the operator enters the designated electrode onto the keyboard and the GUI then highlights the electrode thus selected. In the illustrated embodiment, a circle is flashed around the selected electrode until a next action is taken. FIG. 4(c) illustrates the flowchart of the algorithm that implements the Find Site function. Element 300 accepts a user-entered electrode number (e.g. A4, D3) and returns an entry to a 8×8 matrix associated to the electrodes 16 on structure 14. Element 302 accepts as input the matrix entry and returns the x, y, z coordinates of the user-selected electrode 16. Element 304 draws and flashes a circle around the x, y, z coordinates received from element 302. Element 304 also checks whether any other action is issued by the computer 34. If the answer is yes then it stops the Find Site function and returns to normal screen.

A ZOOM VIEW L function operates, when actuated, to expand the left half-screen to a full screen view.

A ZOOM VIEW R function operates, when actuated, to expand the right half-screen to a full screen view.

A RESET function operates to reset the screen to a default view when actuated.

Various examples of the GUI in use are shown in FIGS. 6, 7, 8 and 9.

Figure 6:
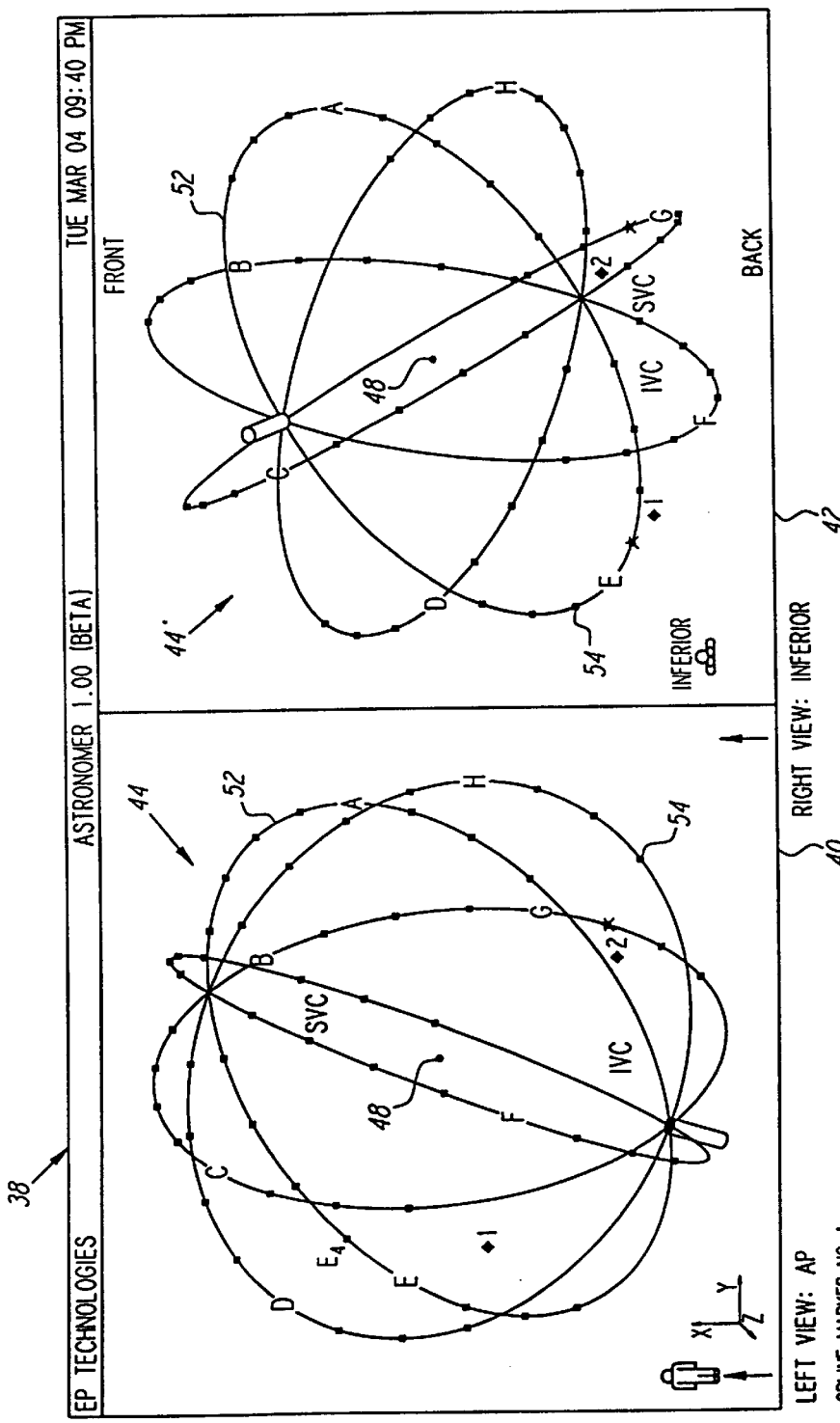
FIG. 6 is a sample of a display screen generated by the GUI showing a multiple electrode structure within the right atrium of a heart for purposes of diagnosing and treating atrial tachycardia within the right atrium.

FIG. 6 represents the multiple electrode structure within the right atrium of the heart. Display panel 40 shows the wire frame image 44 from the AP view, while the right panel 42 shows the image 44' from the inferior view. The relative locations of the Superior Vena Cava and Inferior Vena Cava are marked "SVC" and "IVC" respectively on the displays. A first early activation site is indicated by the marker ♦1, while a second early activation site is indicated by the marker ♦2. The user-entered legend under the display indicates that the first site was ablated at time 09:42:36, while the second site was ablated at time 09:43:02. The legend further indicates that the detected arrhythmia was rendered noninducible following such ablation, thereby indicating a successful treatment.

Figure 7:
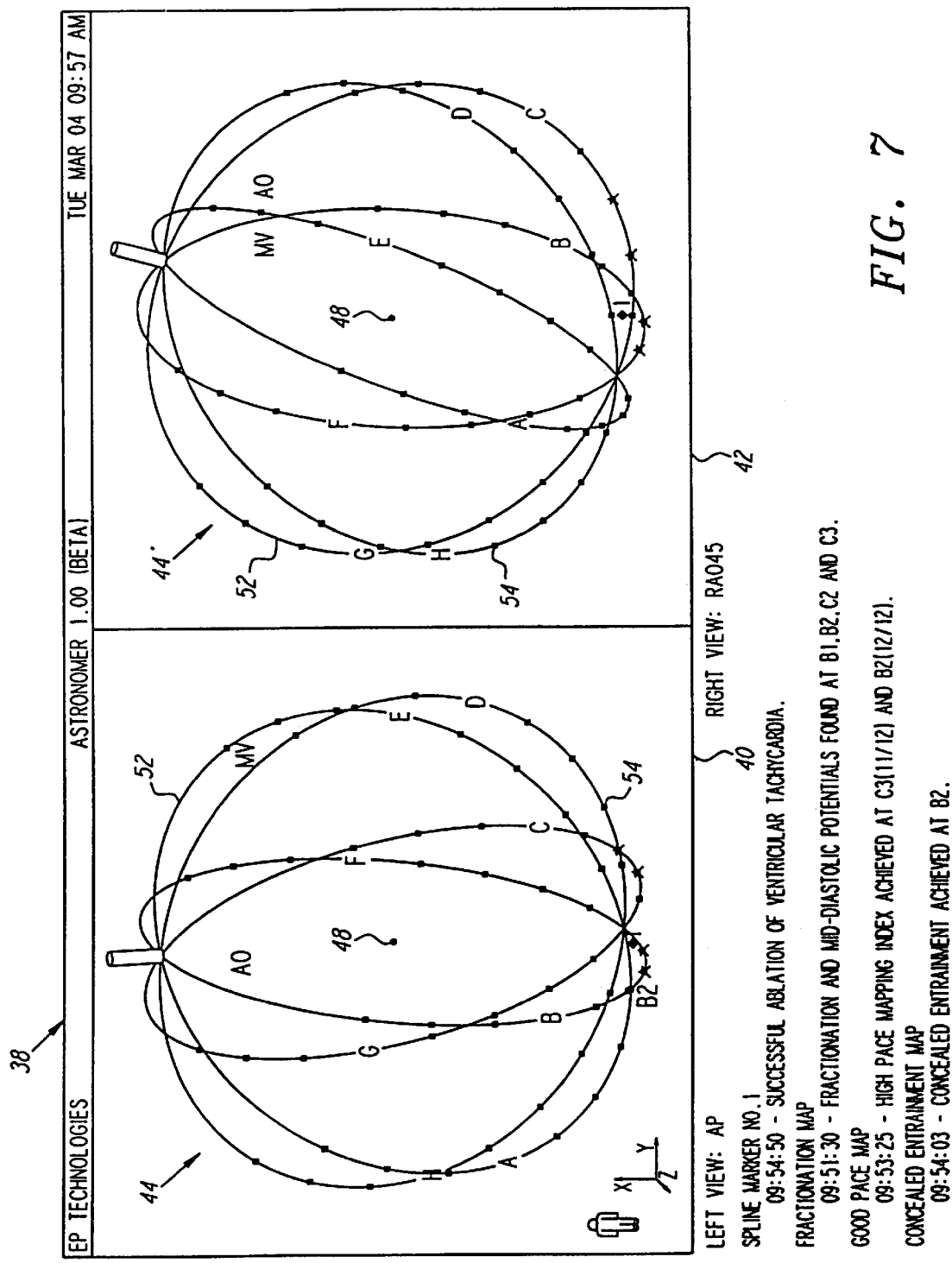
FIG. 7 is a sample of a display screen generated by the GUI showing a multiple electrode structure within the left ventricle of a heart for purposes of diagnosing and treating ventricular tachycardia within the left ventricle.

FIG. 7 represents the multiple electrode structure within the left ventricle for treatment of left ventricular tachycardia. In FIG. 7, the view in the left display panel 40 is from the AP position, while the view in the right panel 42 is from the RAO 45 position. In this example, the various binary mapping functions have been used, and two sites satisfying two or more of the selection criteria have been located and indicated by the symbols ♦, ●, and ★. In particular, two sites exhibiting fractionation and concealed entrainment have been located and identified. Such sites are likely candidates for tissue ablation.

Figure 8:
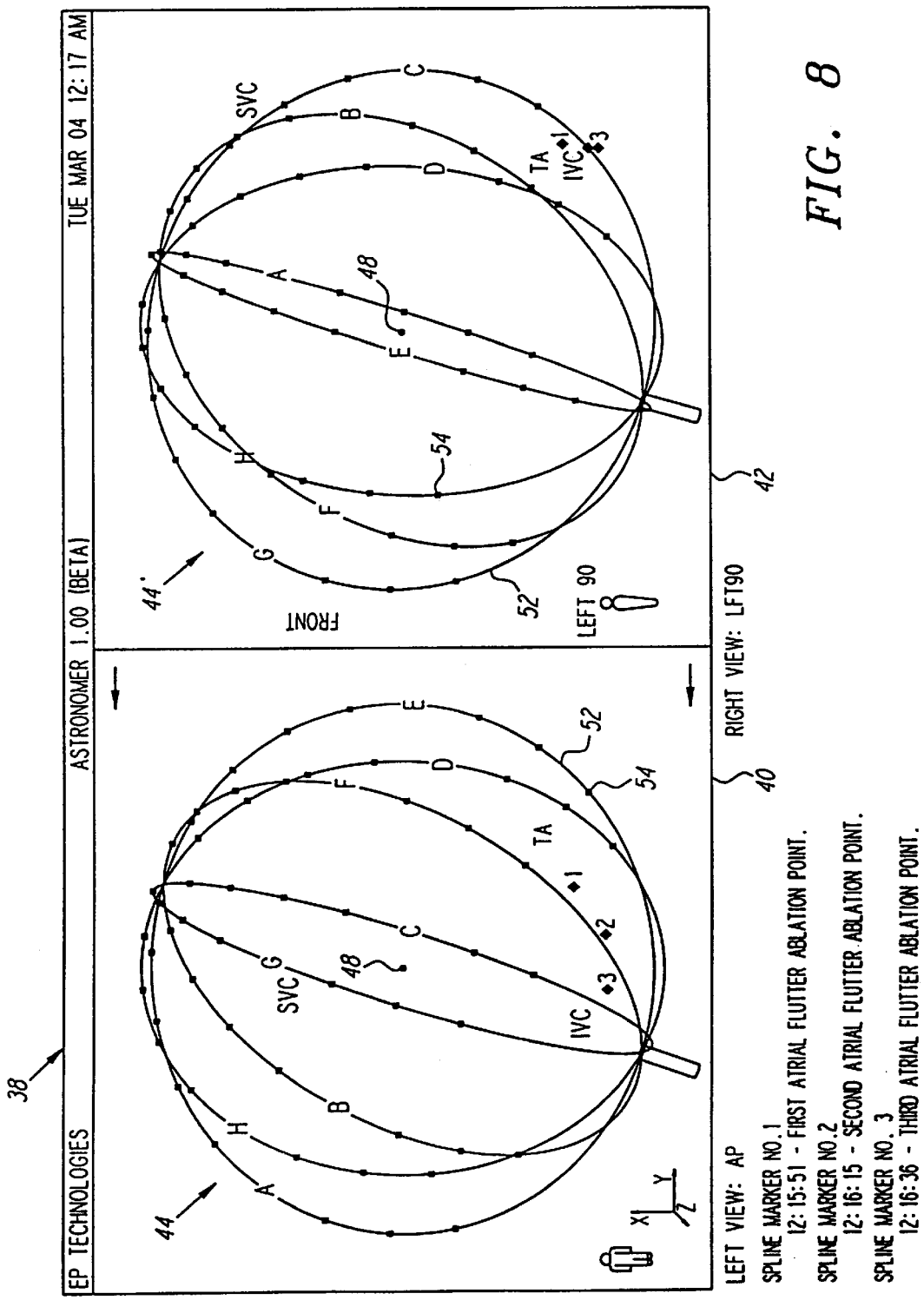
FIG. 8 is a sample of a display screen generated by the GUI showing a multiple electrode structure within the right atrium of a heart for purposes of diagnosing and treating atrial flutter within the right atrium.

FIG. 8 represents the multiple electrode structure within the right atrium for treatment of atrial flutter. The view in the left panel 40 is from the AP position, while the view in the right panel is from the LFT 90 position. Three markers, ♦1, ♦2, and ♦3 are shown in both views. According to the user-entered legend, these markers indicate first, second and third atrial flutter ablation points, respectively.

Figure 9:
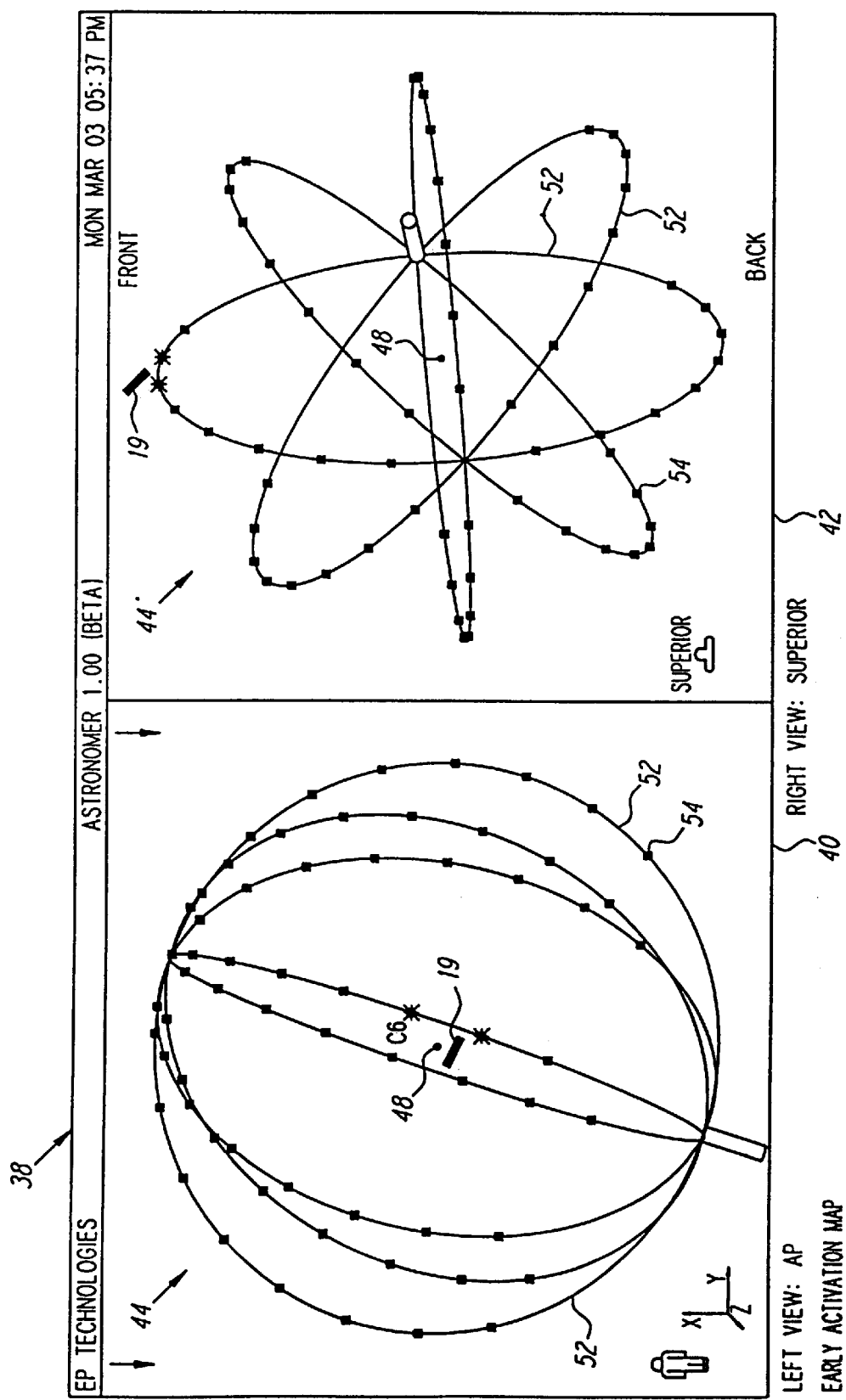
FIG. 9 is a sample of a display screen generated by the GUI showing the location of an ablation electrode during a tachycardia ablation procedure.

FIG. 9 depicts the GUI being used to guide the roving electrode 19. The view in the left panel 40 is from the AP position, while the view in the right panel 42 is from the SUPERIOR position. The relative position of the roving electrode is indicated by the elongate symbol. The highlighted symbols * adjacent the electrodes C6 and C7 indicate early activation sites. The user-entered legend indicates a potential tachycardia ablation site between these electrodes.

The GUI is preferably configured to operate on WINDOWS® compatible laptop or desktop computers. Preferably, the computer should include a 486DX or higher processor operating at a clock frequency of 66 MHZ or higher. A hard disk capacity of 360 MB, and a main memory capacity of 4 MB should be available. Preferably, the GUI is configured to run on WINDOWS® 3.1, WINDOWS 95® or NT operating systems. The GUI is preferably realized as a "C" language program created using known programming techniques.

While a particular embodiment of the invention has been shown and described, it will be obvious to those skilled in the art that changes and modifications can be made without departing from the invention in its broader aspects, and, therefore, the aim in the appended claims is to cover all such changes and modifications as fall within the true spirit and scope of the invention.

We claim:

1. A graphical user interface for generating a visual display depicting a multiple electrode catheter and its relative position and orientation within a body, comprising:

a display screen;

an image generator for generating on the display screen an image of the multiple electrode catheter; and a user-actuable control coupled to the image generator for changing the relative position and orientation of the image as displayed on the display screen to allow for the display of the image from physically unrealized angles.

2. A graphical user interface as defined in claim 1 wherein the user-actuable control further operates to display the image from one or more predetermined viewing angles.

3. A graphical user interface as defined in claim 1 wherein the image generator highlights selected electrodes on the displayed image of the multiple electrode catheter.

4. A graphical user interface as defined in claim 1 wherein the multiple electrode catheter includes a plurality of splines and the image generator function to highlight selected splines of the displayed image.

5. A graphical user interface as defined in claim 1 wherein the image generator displays certain elements of the image at brighter intensity than other elements of the image to enhance the three-dimensional appearance of the displayed image.

6. A graphical user interface as defined in claim 1 wherein the image generator further generates labels associated with at least one electrode of the multiple electrode catheter.

7. A graphical user interface as defined in claim 1 wherein the image generator further generates labels associated with at least one spline of the multiple electrode catheter.

8. A graphical user interface as defined in claim 1 wherein the image generator further generates a label associated with a roving electrode.

9. A graphical user interface as defined in claim 1 wherein the image generator further generates anatomic markers representative of anatomic features within the body.

10. A graphical user interface as defined in claim 1 wherein the image generator further generates user-created markers representative of preidentified events occurring during an electrophysiological procedure.

11. A graphical user interface as defined in claim 1 wherein the user-actuable control is operable to place the anatomic markers at user-selected locations relative to the displayed image.

12. A graphical user interface as defined in claim 1 wherein the image generator further operates to develop iso-value maps in response to physiological data received by individual ones of the electrodes of the multiple electrode catheter.

13. A graphical user interface as defined in claim 1 wherein the image generator displays the position of roving electrodes with respect to the multiple electrode catheter.

14. A graphical user interface as defined in claim 1 wherein the user-actuable control includes the keyboard of a computer.

15. A graphical user interface as defined in claim 1 wherein the graphical user interface comprises a computer and a software program operating on the computer.

16. A graphical user interface for generating a visual display depicting a multiple electrode catheter and its relative position and orientation within a body comprising:

a display screen;

an image generator for generating on the display screen an image of the multiple electrode catheter, wherein the image generator operates to develop binary maps in response to physiological data received by individual ones of the electrodes of the multiple electrode catheter; and a user-actuable control coupled to the image generator for changing the relative position and orientation of the image as displayed on the display screen.

17. A graphical user interface as defined in claim 16 wherein the binary maps are based on the detection of early activation occurrences at one or more electrodes of the multiple electrode catheter.

18. A graphical user interface as defined in claim 16 wherein the binary maps are based on the detection of fractionation occurrences at one or more electrodes of the multiple electrode catheter.

19. A graphical user interface as defined in claim 16 wherein the binary maps are based on the detection of good pace occurrences at one or more electrodes of the multiple electrode catheter.

20. A graphical user interface as defined in claim 16 wherein the binary maps are based on the detection of concealed entrainment occurrences at one or more electrodes of the multiple electrode catheter.

21. A method of utilizing a multiple electrode structure within a body comprising:

locating the multiple electrode structure within a body, displaying the actual multiple electrode structure on an imaging screen, generating and displaying on a second screen an image representing the multiple electrode structure, and changing the displayed orientation of the image until the orientation of the displayed image substantially matches the orientation of the actual multiple electrode structure as displayed on the imaging screen.

22. A method as defined in claim 21, further comprising introducing a roving electrode into the body, and generating and displaying an image representing the roving electrode on the second screen.

23. A method of utilizing a multiple electrode structure within a body comprising:

locating the multiple electrode structure within a body, displaying the actual multiple electrode structure on an imaging screen, generating and displaying on a second screen an image representing the multiple electrode structure, changing the displayed orientation of the image until the orientation of the displayed image substantially matches the orientation of the actual multiple electrode structure as displayed on the imaging screen, and generating and displaying on the second screen binary maps indicative of the presence or absence of predetermined physiological events.

24. A method as defined in claim 23 comprising the further step of generating two or more binary maps representative of the presence or absence of two or more different predetermined physiological events.

25. A method as defined in claim 24 comprising the further step of identifying potential treatment sites by correlating the occurrence of two or more different physiological events at single locations.

* * * * *